(12) United States Patent
Hwang et al.

(10) Patent No.: US 8,815,131 B2
(45) Date of Patent: Aug. 26, 2014

(54) APPARATUS AND METHOD FOR FABRICATING ANTIMICROBIAL HYBRID MATERIALS OF NATURAL PRODUCT AND CARBON NANOMATERIALS

(71) Applicant: Korea Institute of Science and Technology, Seoul (KR)

(72) Inventors: Gi Byoung Hwang, Yeongju-si (KR); Gwi Nam Bae, Seoul (KR); Jae Hee Jung, Cheongju-si (KR); Seung Bok Lee, Seoul (KR); Chu Won Nho, Seoul (KR); Bo Mi Kwon, Seoul (KR)

(73) Assignee: Korea Institute of Science and Technology, Seoul (KR)

( * ) Notice: Subject to any disclaimer, the term of this patent is extended or adjusted under 35 U.S.C. 154(b) by 73 days.

(21) Appl. No.: 13/686,258

(22) Filed: Nov. 27, 2012

(65) Prior Publication Data

US 2013/0161847 A1    Jun. 27, 2013

(30) Foreign Application Priority Data

Dec. 27, 2011    (KR) .................. 10-2011-0143104

(51) Int. Cl.
*B01D 1/18*    (2006.01)
*B29C 35/00*    (2006.01)
*B82Y 40/00*    (2011.01)

(52) U.S. Cl.
CPC ............... *B29C 35/002* (2013.01); *B82Y 40/00* (2013.01); *Y10S 977/892* (2013.01)
USPC ................ 264/14; 264/7; 425/6; 977/892

(58) Field of Classification Search
None
See application file for complete search history.

(56) References Cited

U.S. PATENT DOCUMENTS

| 7,083,747 B2 | 8/2006 | Hampden-Smith et al. |
| 2010/0266694 A1 | 10/2010 | Jennings et al. |

FOREIGN PATENT DOCUMENTS

| KR | 10-2011-0078136 A | 7/2011 |
| KR | 10-2011-0111570 A | 10/2011 |

OTHER PUBLICATIONS

Jung J. H. et al. (2011). "Preparation of Airborne Ag/CNT Hybrid Nanoparticles Using an Aerosol Process and Their Application to Antimicrobial Air Filtration." *Langmuir 2011*. 27. pp. 10256-10264.
Liu, Q. et al. (2012). "Combined on-line Differential Mobility and Particle Mass Analysis for Determination of Size Resolved Particle Density and Microstructure Evolution." *Microporous and Mesoporous Materials*. 153.pp. 210-216 with cover page.

*Primary Examiner* — Mary F Theisen
(74) *Attorney, Agent, or Firm* — NSIP Law

(57) ABSTRACT

The present disclosure relates to an apparatus and a method for fabricating an antimicrobial hybrid material of a natural antimicrobial particle and a carbon nanomaterial, capable of fully utilizing the antimicrobial property of a natural antimicrobial material and a carbon nanomaterial by maximizing adsorption of the natural antimicrobial material on the carbon nanomaterial.

10 Claims, 5 Drawing Sheets

APPARATUS AND METHOD FOR FABRICATING ANTIMICROBIAL HYBRID MATERIALS OF NATURAL PRODUCT AND CARBON NANOMATERIALS

CROSS-REFERENCE TO RELATED APPLICATION

This application claims priority to Korean Patent Application No. 10-2011-143104, filed on Dec. 27, 2011, and all the benefits accruing therefrom under 35 U.S.C. §119, the contents of which in its entirety are herein incorporated by reference.

BACKGROUND

1. Field

The present disclosure relates to an apparatus and a method for fabricating an antimicrobial hybrid material of a natural antimicrobial particle and a carbon nanomaterial. More particularly, the present disclosure relates to an apparatus and a method for fabricating an antimicrobial hybrid material of a natural antimicrobial particle and a carbon nanomaterial, capable of fully utilizing the antimicrobial property of a natural antimicrobial material and a carbon nanomaterial by maximizing adsorption of the natural antimicrobial material on the carbon nanomaterial.

2. Description of the Related Art

With the recent development in nanotechnology, researches are actively made on applications of the nanotechnology in various industries worldwide. In particular, researches on application of nanoparticles to biomaterials, medicine, electronics, chemical catalysts, etc. in various industries are under way. Recently, development of hybrid nanostructure materials for improving applicability and efficiency of these nanoparticles are actively studied. Examples include an antimicrobial fiber in which silver nanoparticles are bound to carbon nanotubes (see Korean Patent Publication No. 2011-78136), a high-efficiency catalyst in which $TiO_2$ particles are bound to carbon nanotubes, or the like. These hybrid nanostructures can exhibit several properties at the same time since they are made up of particles having different properties.

In general, the hybrid nanostructures are fabricated via a chemical process whereby a precipitant or a reducing agent is added to a metal salt so that metal or oxide powder is adhered to a carbon nanotube in an aqueous solution. However, it is difficult to produce a high-purity hybrid nanostructure with this method. Further, since the method involves a complicated process, a long producing-time is required or it is difficult to fabricate the hybrid material continuously.

REFERENCES OF THE RELATED ART

Patent Document (Patent document 1) Korean Patent Publication No. 2011-78136

SUMMARY

The present disclosure is directed to providing an apparatus and a method for fabricating an antimicrobial hybrid material of a natural antimicrobial particle and a carbon nanomaterial, capable of fully utilizing the antimicrobial property of a natural antimicrobial material and a carbon nanomaterial by maximizing adsorption of the natural antimicrobial material on the carbon nanomaterial.

In an aspect, the present disclosure provides an apparatus for fabricating an antimicrobial hybrid material of a natural antimicrobial particle and a carbon nanomaterial, comprising: an antimicrobial hybrid liquid droplet generation unit generating an antimicrobial hybrid liquid droplet by hydraulic pressure spraying a solution comprising a natural antimicrobial material and a carbon nanomaterial; a dehumidifier unit primarily absorbing and removing a solvent component of the antimicrobial hybrid liquid droplet; and a thermal drying unit removing the remaining solvent component of the antimicrobial hybrid liquid droplet discharged from the dehumidifier unit by heating so as to form an antimicrobial hybrid material in which a natural antimicrobial particle is bound to the surface of the carbon nanomaterial, wherein the solution comprising the natural antimicrobial material and the carbon nanomaterial is one in which the carbon nanomaterial is dispersed in a solution in which the natural antimicrobial material is dissolved.

In the solution in which the natural antimicrobial material is dissolved, the natural antimicrobial material is dissolved in a solvent. And, the solution comprising the natural antimicrobial material and the carbon nanomaterial is formed by mixing the solution in which the natural antimicrobial material is dissolved with a solution in which the carbon nanomaterial is dispersed, and the solution in which the natural antimicrobial material is dissolved and the solution in which the carbon nanomaterial is dispersed is mixed at a ratio of 4:1 to 9:1 (wt %). The solvent may be ethanol and the natural antimicrobial material may be one of chitosan, phytoncide, maple leaf extract, *Hosta capitata* extract and *Sophora flavescens* extract.

The apparatus may further comprise a carrier gas supply unit which supplies a carrier gas so as to carry the antimicrobial hybrid liquid droplet and the antimicrobial hybrid material formed by the dehumidifier unit and the thermal drying unit. The apparatus may further comprise a collection unit collecting the antimicrobial hybrid material at a rear end of the thermal drying unit, and the collection unit may be one of a filter, an impactor and a cyclone.

The dehumidifier unit may comprise a chamber and a dehumidifier provided in the chamber, and the dehumidifier may be one of silica gel and activated carbon. The carbon nanomaterial may be one of carbon nanotube, graphene, carbon fiber and carbon nylon.

In another aspect, the present disclosure provides a method for fabricating an antimicrobial hybrid material of a natural antimicrobial particle and a carbon nanomaterial, comprising: mixing a solution in which a natural antimicrobial material is dissolved with a solution in which a carbon nanomaterial is dispersed; hydraulic pressure spraying the mixed solution so as to form an antimicrobial hybrid liquid droplet comprising the natural antimicrobial particle and the carbon nanomaterial; primarily removing a solvent component of the antimicrobial hybrid liquid droplet using a dehumidifier unit; and removing the remaining solvent component of the antimicrobial hybrid liquid droplet discharged from the dehumidifier unit by heating so as to form an antimicrobial hybrid material in which a natural antimicrobial particle is bound to the surface of the carbon nanomaterial.

The apparatus and method for fabricating an antimicrobial hybrid material of a natural antimicrobial particle and a carbon nanomaterial according to the present disclosure provide the following advantageous effects.

By fabricating an antimicrobial hybrid material in which a natural antimicrobial particle is bound to the surface of a carbon nanomaterial, an antimicrobial agent with various antimicrobial properties can be obtained. Further, by improving binding to the carbon nanomaterial using a natural antimicrobial material soluble in a solvent, waste of the natural antimicrobial material can be prevented.

BRIEF DESCRIPTION OF THE DRAWINGS

The above and other aspects, features and advantages of the disclosed exemplary embodiments will be more apparent from the following detailed description taken in conjunction with the accompanying drawings in which.

[Detailed Description of Main Elements]

110: carrier gas supply unit
120: antimicrobial hybrid liquid droplet generation unit
130: dehumidifier unit        140: thermal drying unit
150: collection unit

DETAILED DESCRIPTION

The present disclosure relates to fabrication of an antimicrobial hybrid material in which a natural antimicrobial particle is bound to a carbon nanomaterial, which is fabricated by dispersing a carbon nanomaterial in a solvent and dissolving a natural antimicrobial material in the solvent so that a natural antimicrobial particle is extracted from the natural antimicrobial material, hydraulic pressure spraying the solution comprising the natural antimicrobial particle and the carbon nanomaterial so as to form an antimicrobial hybrid liquid droplet, and removing a solvent component from the liquid droplet so as to form an antimicrobial hybrid material in which the natural antimicrobial particle is bound to the surface of the carbon nanomaterial. Since the natural antimicrobial particle is extracted from the dissolved natural antimicrobial material and is bound to the surface of the carbon nanomaterial, the natural antimicrobial material can be fully utilized and the binding to the carbon nanomaterial can be maximized. Hereinafter, an apparatus and a method for fabricating an antimicrobial hybrid material of a natural antimicrobial material and a carbon nanomaterial according to an exemplary embodiment of the present disclosure will be described in detail referring to the attached drawings.

Figure 1:
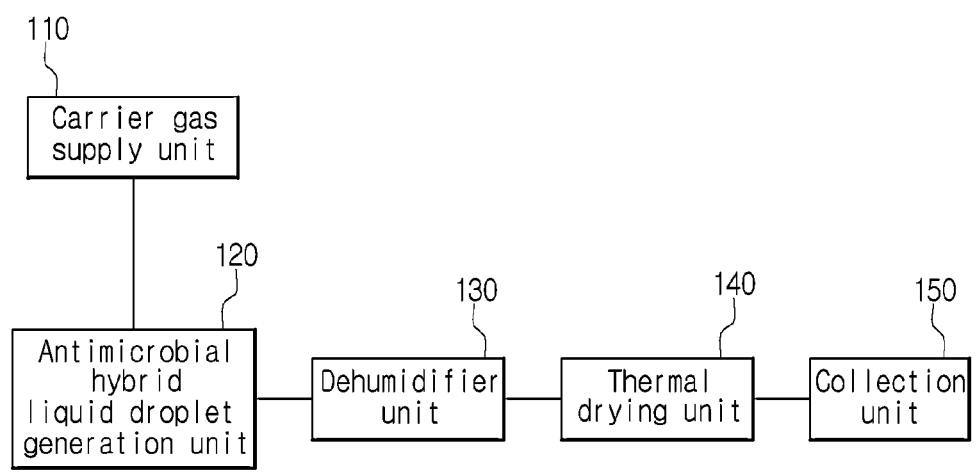
FIG. 1 is a block diagram of an apparatus for fabricating an antimicrobial hybrid material of a natural antimicrobial particle and a carbon nanomaterial according to an exemplary embodiment of the present disclosure.

Referring to FIG. 1, an apparatus for fabricating an antimicrobial hybrid material of a natural antimicrobial material and a carbon nanomaterial according to an exemplary embodiment of the present disclosure comprises a carrier gas supply unit 110, an antimicrobial hybrid liquid droplet generation unit 120, a dehumidifier unit 130, a thermal drying unit 140 and a collection unit 150.

The carrier gas supply unit 110, the antimicrobial hybrid liquid droplet generation unit 120, the dehumidifier unit 130, the thermal drying unit 140 and the collection unit 150 are disposed in an in-line configuration. Accordingly, the fabrication of the antimicrobial hybrid material according to the present disclosure is carried out by a series of continuous processes.

The carrier gas supply unit 110 supplies a carrier gas. The carrier gas is transported through the antimicrobial hybrid liquid droplet generation unit 120, the dehumidifier unit 130, the thermal drying unit 140 and the collection unit 150. It serves to transport an antimicrobial hybrid liquid droplet formed by the antimicrobial hybrid liquid droplet generation unit 120 and an antimicrobial hybrid material dried by the dehumidifier unit 130 and the thermal drying unit 140. The carrier gas may be an inert gas such as nitrogen, argon, etc.

The antimicrobial hybrid liquid droplet generation unit 120 pressure sprays a solution comprising a natural antimicrobial particle and a carbon nanomaterial so as to generate the antimicrobial hybrid liquid droplet. The solution comprising the natural antimicrobial particle and the carbon nanomaterial is prepared by mixing a solution in which the natural antimicrobial material is dissolved and a solution in which the carbon nanomaterial is dispersed.

In the present disclosure, the natural antimicrobial material should be necessarily dissolved in a solvent, since the natural antimicrobial particle should be extracted from the natural antimicrobial material, which is an organic material comprising the natural antimicrobial particle, and the extraction of the natural antimicrobial particle from the natural antimicrobial material can be achieved by dissolving the natural antimicrobial material in a solvent. Accordingly the natural antimicrobial material used in the present disclosure should be dissoluble in a solvent, and the solvent may be ethanol. Examples of the natural antimicrobial material that can be dissolved in ethanol include chitosan, phytoncide, maple leaf extract, *Hosta capitata* extract, *Sophora flavescens* extract, and so forth.

Accordingly, in the solution comprising the natural antimicrobial material and the carbon nanomaterial, the natural antimicrobial material is in dissolved state and the carbon nanomaterial is in dispersed state. In other words, it can be said that the carbon nanomaterial is dispersed in a solution in which the natural antimicrobial material is dissolved. The carbon nanomaterial may be carbon nanotube, graphene, carbon fiber or carbon nylon.

When the solution comprising the natural antimicrobial particle extracted from the natural antimicrobial material and the carbon nanomaterial is pressure sprayed by the antimicrobial hybrid liquid droplet generation unit 120, the antimicrobial hybrid liquid droplet comprising the natural antimicrobial particle and the carbon nanomaterial is formed. The antimicrobial hybrid liquid droplet generated by the antimicrobial hybrid liquid droplet generation unit 120 has a size of sub-micron scale.

Although a hybrid nanostructure in which a silver nanoparticle is bound to a carbon nanotube is disclosed in the prior art, since the silver nanoparticle is not dissolved in a solvent, the binding efficiency of the silver nanoparticle to the carbon nanotube is very poor when a hybrid nanostructure is formed by dispersing the silver nanoparticle and the carbon nanotube in a solvent according to the method of the present disclosure.

The dehumidifier unit 130 serves to primarily remove a solvent component of the antimicrobial hybrid liquid droplet. Specifically, it may comprise a chamber having a predetermined volume and a dehumidifier provided in the chamber. The dehumidifier provided in the chamber may be silica gel, activated carbon, etc. The antimicrobial hybrid liquid droplet generated by the antimicrobial hybrid liquid droplet generation unit 120 is transported to the dehumidifier unit 130 by the carrier gas, and the solvent component of the antimicrobial hybrid liquid droplet is primarily removed as the antimicrobial hybrid liquid droplet passes through the dehumidifier unit 130.

The thermal drying unit 140 serves to completely remove the solvent component remaining in the antimicrobial hybrid liquid droplet discharged from the dehumidifier unit 130. It may comprise an electrical heating tube having predetermined length and volume and controlled to a predetermined temperature. The solvent component remaining in the antimicrobial hybrid liquid droplet may be removed by passing the antimicrobial hybrid liquid droplet through the electrical heating tube. When the solvent component is removed from the antimicrobial hybrid liquid droplet, only the natural antimicrobial particle and the carbon nanomaterial remain. Since both the natural antimicrobial particle and the carbon nanomaterial have nano-scale sizes, they bind with each other by the van der Waals adhesive force. As a result, an antimicrobial hybrid material in which the natural antimicrobial particle is bound to the carbon nanomaterial is formed. The thermal drying unit 140 may be controlled in a temperature range of 75-100° C. At temperatures below 75° C., the solvent may not be removed rapidly. And, at temperatures above 100° C., the natural antimicrobial material may be degraded.

The collection unit 150 is provided at a rear end of the thermal drying unit 140 and serves to collect the antimicrobial hybrid material. For this, the collection unit 150 may be configured as a filter, an impactor, a cyclone, etc. capable of collecting particulate materials.

An apparatus and a method for fabricating an antimicrobial hybrid material of a natural antimicrobial particle and a carbon nanomaterial according to an exemplary embodiment of the present disclosure were described above. Hereinafter, the properties of a natural antimicrobial particle, a carbon nanotube and an antimicrobial hybrid material fabricated according to an exemplary embodiment of the present disclosure will be described.

Figure 2:
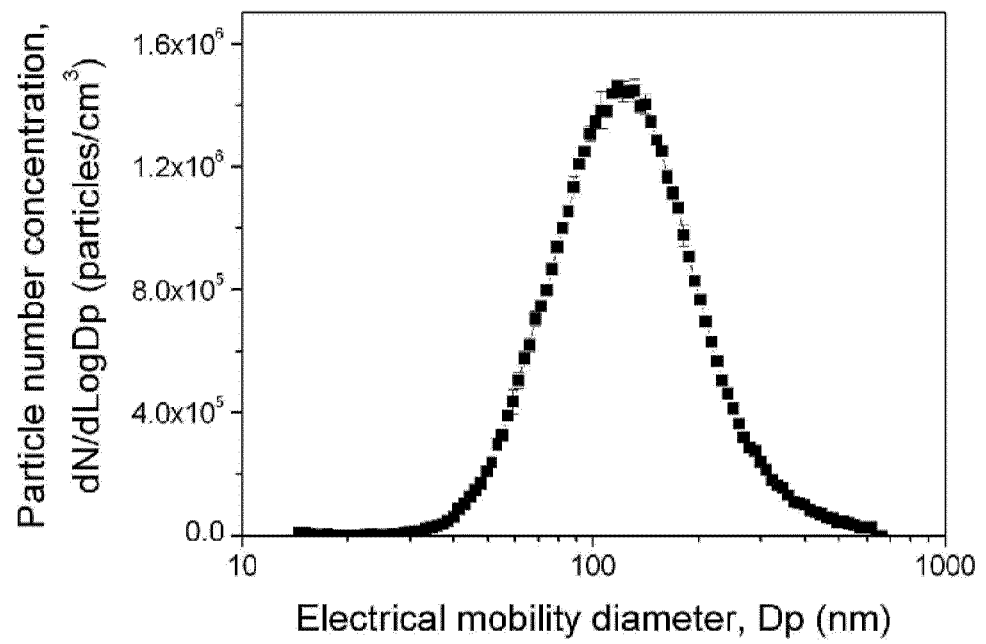
FIG. 2 shows a particle size distribution of an antimicrobial hybrid material fabricated according to an exemplary embodiment of the present disclosure.

FIG. 2 shows a particle size distribution of an antimicrobial hybrid material in which a natural antimicrobial metal particle is bound to a carbon nanotube fabricated according to an exemplary embodiment of the present disclosure. The experimental condition of FIG. 2 is as follows. 20 mL of a 1:5 mixture solution of a solution of a carbon nanotube and a solution of *Sophora flavescens* extract was added to an antimicrobial hybrid liquid droplet generation unit and pressure sprayed while supplying a carrier gas to the antimicrobial hybrid liquid droplet generation unit at 1 L/min so as to generate an antimicrobial hybrid liquid droplet. The generated antimicrobial hybrid liquid droplet was sequentially passed through a dehumidifier unit in which activated carbon is provided and a high-temperature electrical tube furnace so as to fabricate an antimicrobial hybrid material in which a *Sophora flavescens* extract particle is bound to the surface of the carbon nanotube.

Referring to FIG. 2, it can be seen that the fabricated antimicrobial hybrid material has a unimodal particle size distribution, with highest frequency at about 112 nm.

Figure 3A:
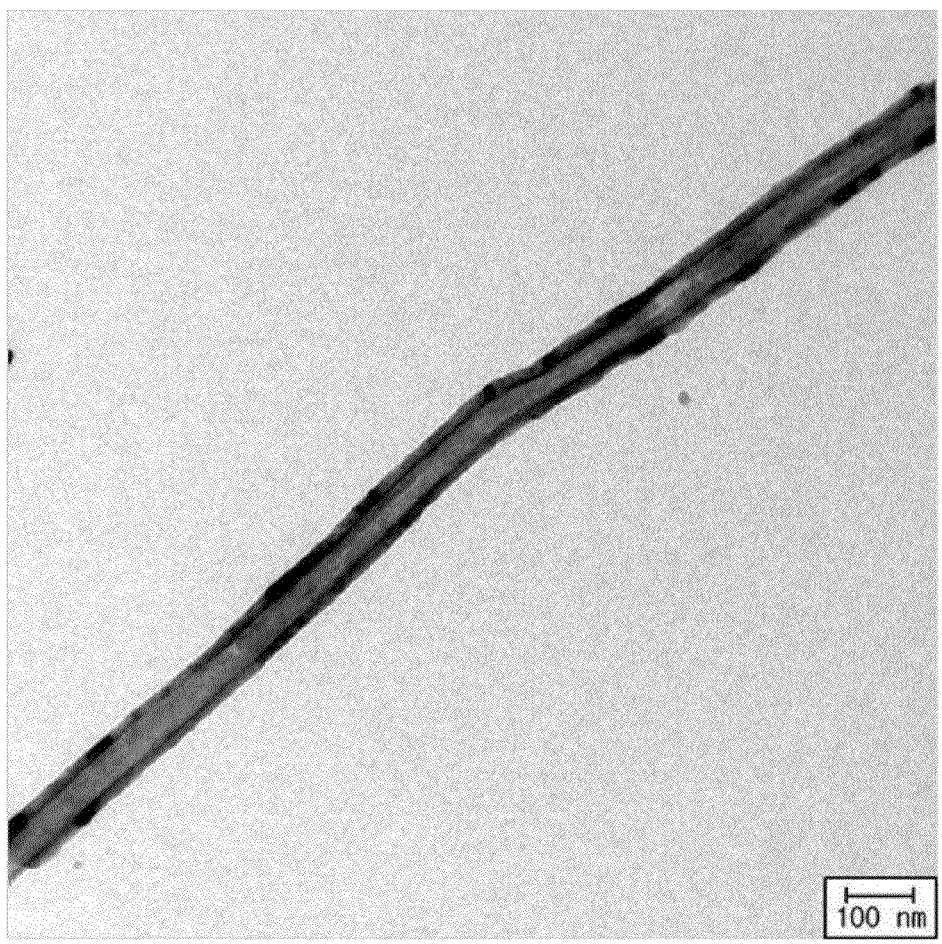
FIGS. 3a-3c are scanning electron microscopic images of a carbon nanotube, a *Sophora flavescens* extract particle and an antimicrobial hybrid material.
Figure 3B:
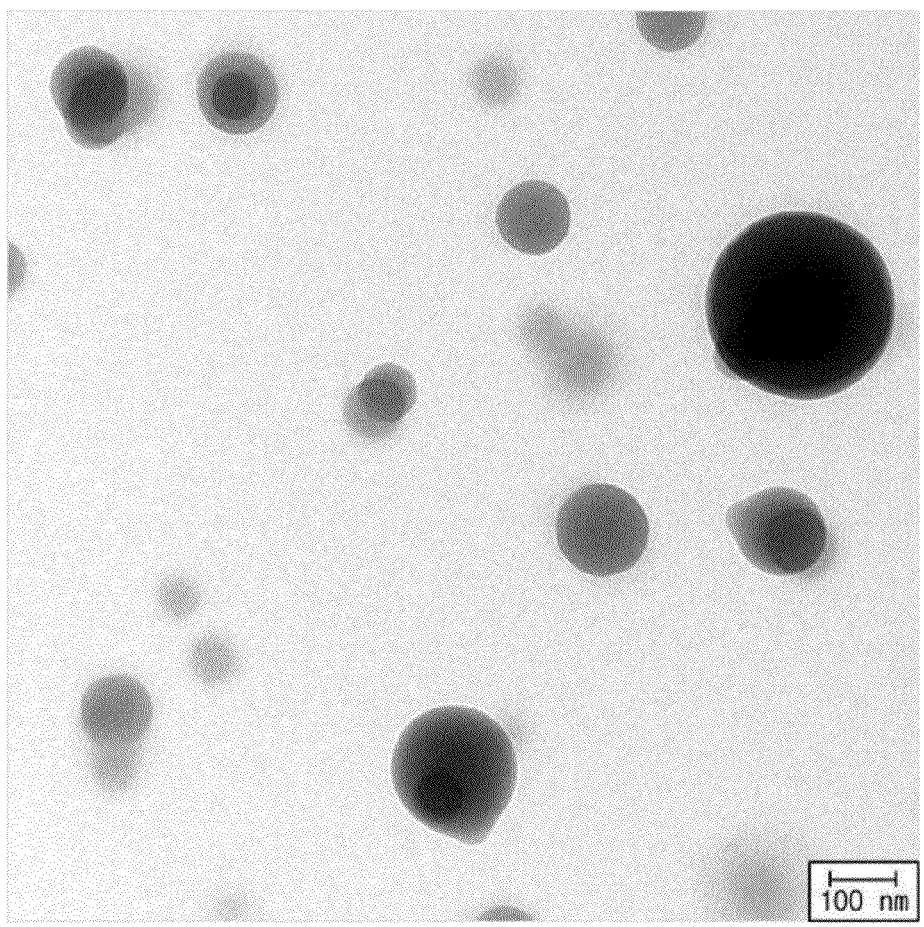
Figure 3C:
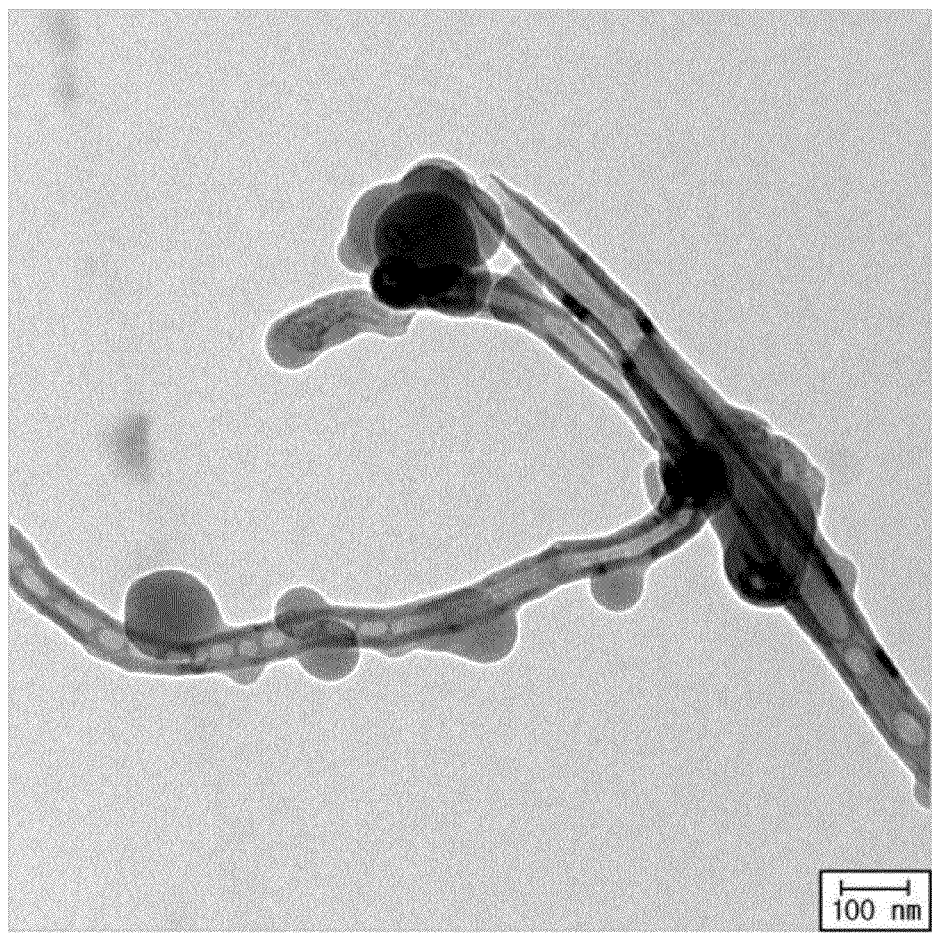

FIGS. 3a-3c are scanning electron microscopic images of the carbon nanotube, the *Sophora flavescens* extract particle and the antimicrobial hybrid material. Referring to FIG. 3c, it can be seen that the natural antimicrobial particle, i.e. the *Sophora flavescens* extract particle, is uniformly distributed on the surface of the carbon nanotube.

While the exemplary embodiments have been shown and described, it will be understood by those skilled in the art that various changes in form and details may be made thereto without departing from the spirit and scope of the present disclosure as defined by the appended claims.

What is claimed is:

1. An apparatus for fabricating an antimicrobial hybrid material of a natural antimicrobial particle and a carbon nanomaterial, comprising:
    an antimicrobial hybrid liquid droplet generation unit generating an antimicrobial hybrid liquid droplet by hydraulic pressure spraying a solution comprising a natural antimicrobial material and a carbon nanomaterial;
    a dehumidifier unit primarily absorbing and removing a solvent component of the antimicrobial hybrid liquid droplet; and
    a thermal drying unit removing the remaining solvent component of the antimicrobial hybrid liquid droplet discharged from the dehumidifier unit by heating so as to form an antimicrobial hybrid material in which a natural antimicrobial particle is bound to the surface of the carbon nanomaterial,
    wherein the solution comprising the natural antimicrobial material and the carbon nanomaterial is one in which the carbon nanomaterial is dispersed in a solution in which the natural antimicrobial material is dissolved.

2. The apparatus for fabricating an antimicrobial hybrid material of a natural antimicrobial particle and a carbon nanomaterial according to claim 1, wherein, in the solution in which the natural antimicrobial material is dissolved, the natural antimicrobial material is dissolved in a solvent.

3. The apparatus for fabricating an antimicrobial hybrid material of a natural antimicrobial particle and a carbon nanomaterial according to claim 1, wherein the solution comprising the natural antimicrobial material and the carbon nanomaterial is formed by mixing the solution in which the natural antimicrobial material is dissolved with a solution in which the carbon nanomaterial is dispersed, and the solution in which the natural antimicrobial material is dissolved and the solution in which the carbon nanomaterial is dispersed is mixed at a ratio of 4:1 to 9:1 (wt %).

4. The apparatus for fabricating an antimicrobial hybrid material of a natural antimicrobial particle and a carbon nanomaterial according to claim 2, wherein the solvent is ethanol and the natural antimicrobial material is one of chitosan, phytoncide, maple leaf extract, *Hosta capitata* extract and *Sophora flavescens* extract.

5. The apparatus for fabricating an antimicrobial hybrid material of a natural antimicrobial particle and a carbon nanomaterial according to claim 1, wherein the apparatus further comprises a carrier gas supply unit, the carrier gas supply unit supplying a carrier gas so as to carry the antimicrobial hybrid liquid droplet and the antimicrobial hybrid material formed by the dehumidifier unit and the thermal drying unit.

6. The apparatus for fabricating an antimicrobial hybrid material of a natural antimicrobial particle and a carbon nanomaterial according to claim 1, wherein the apparatus further comprises a collection unit collecting the antimicrobial hybrid material at a rear end of the thermal drying unit, the collection unit being one of a filter, an impactor and a cyclone.

7. The apparatus for fabricating an antimicrobial hybrid material of a natural antimicrobial particle and a carbon nanomaterial according to claim 1, wherein the dehumidifier unit comprises a chamber and a dehumidifier provided in the chamber, the dehumidifier being one of silica gel and activated carbon.

8. The apparatus for fabricating an antimicrobial hybrid material of a natural antimicrobial particle and a carbon nanomaterial according to claim 1, wherein the carbon nanomaterial is one of carbon nanotube, graphene, carbon fiber and carbon nylon.

9. A method for fabricating an antimicrobial hybrid material of a natural antimicrobial particle and a carbon nanomaterial, comprising:
- mixing a solution in which a natural antimicrobial material is dissolved with a solution in which a carbon nanomaterial is dispersed;
- hydraulic pressure spraying the mixed solution so as to form an antimicrobial hybrid liquid droplet comprising the natural antimicrobial particle and the carbon nanomaterial;
- primarily removing a solvent component of the antimicrobial hybrid liquid droplet using a dehumidifier unit; and
- removing the remaining solvent component of the antimicrobial hybrid liquid droplet discharged from the dehumidifier unit by heating so as to form an antimicrobial hybrid material in which a natural antimicrobial particle is bound to the surface of the carbon nanomaterial.

10. The method for fabricating an antimicrobial hybrid material of a natural antimicrobial particle and a carbon nanomaterial according to claim 9, wherein the solution in which the natural antimicrobial material is dissolved and the solution in which the carbon nanomaterial is dispersed is mixed at a ratio of 4:1 to 9:1 (wt %).

\* \* \* \* \*